United States Patent
Del Soldato

(10) Patent No.: US 7,160,871 B2
(45) Date of Patent: *Jan. 9, 2007

(54) NITRATE ESTERS OF CORTICOID COMPOUNDS AND PHARMACEUTICAL APPLICATIONS THEREOF

(75) Inventor: Piero Del Soldato, Milan (IT)

(73) Assignee: Nicox S.A., Sophia Antipolis (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/374,220

(22) Filed: Mar. 14, 2006

(65) Prior Publication Data

US 2006/0154905 A1 Jul. 13, 2006

Related U.S. Application Data

(62) Division of application No. 10/462,637, filed on Jun. 17, 2003, now Pat. No. 7,056,905, which is a division of application No. 09/269,729, filed as application No. PCT/EP97/05426 on Oct. 2, 1997, now Pat. No. 6,610,676.

(30) Foreign Application Priority Data

Oct. 4, 1996 (IT) .............................. MI96A2048

(51) Int. Cl.
*A61K 31/56* (2006.01)
*C07J 41/00* (2006.01)

(52) U.S. Cl. ................... 514/179; 514/178; 552/575
(58) Field of Classification Search ............. 552/575; 514/178, 179
See application file for complete search history.

(56) References Cited

U.S. PATENT DOCUMENTS

| | | | |
|---|---|---|---|
| 2,990,401 A | 6/1961 | Bernstein et al. | |
| 3,183,252 A | 5/1965 | Crabbe | |
| 3,209,000 A | 9/1965 | Babcock et al. | |
| 3,494,941 A | 2/1970 | Ledig et al. | |
| 5,824,669 A | 10/1998 | Garvey et al. | |
| 5,837,698 A | 11/1998 | Tjoeng et al. | |
| 6,197,762 B1 | 3/2001 | Garvey et al. | |
| 6,579,863 B1 | 6/2003 | Garvey et al. | |
| 7,056,905 B1 * | 6/2006 | Del Soldato | 514/178 |
| 2003/0199529 A1 | 10/2003 | Garvey et al. | |

FOREIGN PATENT DOCUMENTS

| | | |
|---|---|---|
| DE | 1 643 034 | 5/1971 |
| DE | 2 222 491 A | 11/1972 |
| FR | 1 561 908 | 2/1969 |
| FR | 2 274 309 | 1/1976 |
| GB | 1 544 512 | 4/1979 |
| WO | 94/04484 A1 | 3/1994 |
| WO | 94/12463 A1 | 6/1994 |
| WO | 95/09831 A1 | 4/1995 |
| WO | 95/30641 A1 | 11/1995 |
| WO | 97/34871 A1 | 9/1997 |
| WO | 97/40836 A1 | 11/1997 |
| WO | 97/41144 A1 | 11/1997 |

OTHER PUBLICATIONS

"Goodman & Gilman's The Pharmacological Basis of Therapeutics", 9th Edition, 1996, pp. 1459-1465.
"Goodman & Gilman's The Pharmacological Basis of Therapeutics", 9th Edition, 1996, p. 1474.
"The Merck Index", 12th Edition, 1996.
Martindale "The Extrapharmacopeia", 30th Edition, 1993, pp. 712-723.
"Anti-Inflammatory Potency and Gastrointestinal Toxicity of a New Compound, Nitronaproxen", Cuzzolin et al, *Pharmacological Research*, vol. 31, No. 1, 1995, pp. 61-65.
"Influence of Fasting and Cimetidine on the Relationship between Ulcerogenic and Anti-Inflammatory Properties of Indomethacin", Del Soldato et al, *Br. J. Pharmac.*, 67, 1979, pp. 33-37.
"Feedback Inhibition of Nitric Oxide Synthase Activity by Nitric Oxide", Assreuy et al, *Br. J. Pharmacol.*, 108, 1993, pp. 833-837.
"Influence of Dexamethasone on the Regional Haemodynamic Responses to Lipopolysaccharide in Conscious Rats: Effects of the Non-Selective Endothelin Antagonist, SB 209670", Gardiner et al, *Br. J. Pharmacol.*, 117, 1996, 49P.
"Quantitative in-vivo Studies on Angiogenesis in a Rat Sponge Model", Andrade et al, *Br. J. exp. Path.*, 68, 1987, pp. 755-766.
"Correlation of $^{133}$Xe Clearance, Blood Flow and Histology in the Rat Sponge Model for Angiogenesis", Hu et al, *Laboratory Investigation*, vol. 72, No. 5, 1995, pp. 601-610.

(Continued)

*Primary Examiner*—Barbara P. Badio
(74) *Attorney, Agent, or Firm*—Arent Fox PLLC

(57) ABSTRACT

Compounds of the formula

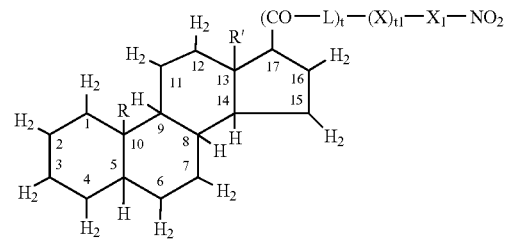

and use of the compounds as medicaments.

2 Claims, No Drawings

OTHER PUBLICATIONS

"The Effect of Glucocorticoids on Osteoblast Function", Doherty et al, *The Journal of Bone and Joint Surgery*, Series A77/3, 1995, pp. 396-404.

"Synthesis and Biological Activity of Alkyl Succinates of Prednisolone", Bayunova et al, *Pharmaceutical Chemistry Journal*, vol. 14, No. 12, 1981, pp. 878-880.

"1,4:3,6-Dianhydrohexitol Nitrate Derivatives. II [1)]Synthesis and Antianginal Activity of Aryl- or Arylcarbonylpiperazine Derivatives[2)]", Hayashi et al, *Chem. Pharm. Bull.*, vol. 41, No. 6, Jun. 1993, pp. 1100-1110.

"Nitrate Esters of Steroid Hormones and Related Compounds, Preparation and Biological Properties", Hodosan et al, *Arzneimittel Forschung. Drug Research.*, vol. 19, No. 4, 1969, pp. 684-685.

"Design of Ligands for the Glucocorticoid and Progestin Receptors", Teutsch et al, *Biochem. Soc. Trans.*, vol. 19, No. 4, 1991, pp. 901-908.

"Synthesis of 5-pregnene-3β,17α-diol-20-one 3-acetate 17α-carboxylic acid esters, and studies on their structure-activity relations", *Chemical Abstracts*, vol. 099, No. 11, Sep. 12, 1983, Abstract No. 088460.

"Synthesis of 3β-hydroxypregn-5-en-20-one A and B ring derivatives and studies on their structure-activity relationships", *Chemical Abstracts*, vol. 097, No. 11, Sep. 13, 1982, Abstract No. 092623.

"16-Hydroxylated Steroids, XXII.[1] The Preparation of the 16-Methyl Ether of Triamcinolone[2]", Heller et al, *Journal of Organic Chemistry*, vol. 27, No. 1, Jan. 18, 1962, pp. 328-331.

"Antiphlogistic pregnane derivatives", *Chemical Abstracts*, vol. 070, No. 15, Apr. 14, 1969, Abstract No. 068654.

\* cited by examiner

NITRATE ESTERS OF CORTICOID COMPOUNDS AND PHARMACEUTICAL APPLICATIONS THEREOF

This application is a divisional of prior application Ser. No. 10/462,637, filed Jun. 17, 2003, now U.S. Pat. No. 7,056,905 B2; which is a divisional of application Ser. No. 09/269,729, filed Apr. 2, 1999, now U.S. Pat. No. 6,610,676 B1, which in turn was a National Stage application of International Application No. PCT/EP97/05426, filed Oct. 2, 1997. The disclosures of the prior applications are hereby incorporated by reference herein in their entirety.

The present invention relates to preparation of new corticoid compounds.

In particular it relates to steroid-structured compounds having anti-inflammatory, immunodepressive and angiostatic activities (the so-called steroid anti-inflammatory drugs).

The compounds according to the present invention are therapeutically useful in the treatment of pathologic conditions where generally corticosteroid (corticoids) preparations are used, but with increased benefits.

This represents an unexpected advantage over the known corticoids products. In fact, by taking into account the various defined therapeutic uses of a specific product, it is always possible, with the new products of the present invention, to find a better combination of results with respect to the known corticoids. Contrary to any expectation the products of the present invention are characterised by the fact that they show an improved therapeutic profile: high activity combined with low side-effects.

Corticoids are well known as a first-choice pharmacological measure in the treatment of inflammatory disease. Drugs in this category—which include, for example, hydrocortisone, cortisone, prednisolone, prednisone, fludrocortisone, desoxycorticosterone, methylprednisolone, triamcinolone, paramethasone, betametasone, dexamethasone, triamcinolone acetonide, fluocinolone acetonide, beclomethasone, acetoxypregnelone, etc.—have marked pharmacotoxicological effects on various organs. Because of this, the clinical use and discontinued use thereof cause a series of side effects, some of which are very severe. See for example Goodman & Gilman: "The Pharmaceutical Basis of Therapeutics", 9th Ed., pages 1459–1465, 1996.

These toxic effects include:
- those on bone which lead to changed cell metabolism and a high frequency of osteoporosis;
- those on the cardiovascular system which cause hypertensive reactions;
- those on the gastrointestinal tract which cause gastric damage.

See for instance Martindale: "The Extrapharmacopoeia", 30th Ed., pages 712–723, 1993.

According to the above mentioned art it appears to be almost impossible for therapeutic activities to be separated from side effects, see Goodman et al., as mentioned above, at page 1474.

Known in the art are non-steroid anti-inflammatory drugs either with or without acidic ending, see patents WO 94/04484, WO 94/12463, WO 95/09831, WO 95/30641 for non-acidic ending and the patents therein mentioned for those with acidic ending.

However, it should be noted that steroid compounds are completely different from non-steroid compounds chemically, pharmacologically and biochemically as the pharmaco-toxicological mechanism of action of non-steroid products is based on inhibition of one or more cyclo-oxygenases (COX), while steroid products have nothing to share with COX and have more complex pharmaco-toxicological mechanisms of action which have not yet been fully explained.

It is well known that these two groups of compounds are listed in completely separate categories in international pharmacopoeias.

The applicant has surprisingly and unexpectedly found corticosteroids (corticoids) which are very effective, even superior to those in the known art, and have, at the same time, a higher tolerance than the known corticoids as unexpectedly they do not cause the above side effects, or when they do, these are lower.

An object of the present invention are corticosteroids and their use as anti-inflammatory, immunosuppressive and angiostatic agents having the general formula:

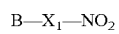

or their esters or salts, where:

B has the following structure:

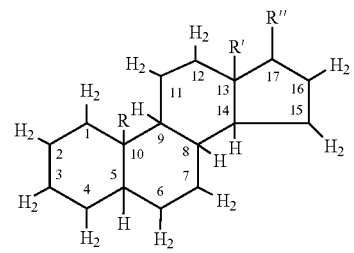

where, in place of the hydrogens H in the CH group or two hydrogens $H_2$ in the $CH_2$ group shown in the general formula, there may be the following substituents:

at position 1-2: there may be a double bond;
at position 2-3: there may be the following substituent:

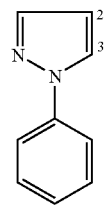

at position 2: there may be Cl, Br;
at position 3: there may be CO, —O—$CH_2$—$CH_2$—Cl, OH;
at position 4-5: there may be a double bond;
at position 5-6: there may be a double bond;
at position 6: there may be Cl, F, $CH_3$, —CHO;
at position 7: there may be Cl;
at position 9: there may be Cl, F;
at position 11: there may be OH, CO, Cl;
at position 16, there may be $CH_3$, OH, =$CH_2$;
at position 17: there may be OH, $CH_3$, OCO(O)$_{ua}$($CH_2$)$_{va}$$CH_3$, or

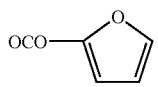

where ua is an integer equal to 0 or 1, va is an integer from 0 to 4;

at positions 16-17: there may be the following groups

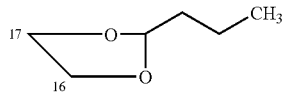

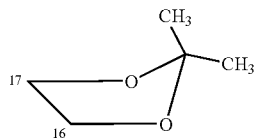

R and R' are equal or different one from the other and may be hydrogen or linear or branched alkyls having from 1 to 4 carbon atoms, preferably R=R'=CH$_3$;

B being a corticosteroid residue;

R" is —(CO-L)$_t$—(X)$_{t1}$— where t and t1 are integers equal or different one from the other and equal to 0 or 1, provided that they cannot be both equal to 0 when B contains no —OH groups;

the bivalent bridging group L is selected from:

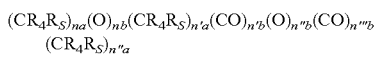

where na, n' and n"a are equal or different one from the other and are integers from 0 to 6, preferably from 1 to 3; nb, nb', n"b and n'"b are equal or different one from the other and are integers equal to 0 or 1; $R_4$ and $R_S$ are equal or different one from the other and are chosen from H, linear or branched alkyl having from 1 to 5 carbon atoms, preferably from 1 to 3;

X is equal to $X_0$=O, NH, $NR_{1C}$ where $R_{1C}$ is a linear or branched alkyl having from 1 to 10 C atoms; or equal to $X_2$ where $X_2$ is equal to OH, CH$_3$, Cl, N(—CH$_2$—CH$_3$)$_2$, SCH$_2$F, SH,

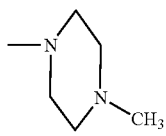

$X_1$ is a bivalent connecting bridge chosen from:

YO where Y is a linear or whenever possible branched C$_1$-C$_{20}$ alkylene, preferably having from 2 to 5 carbon atoms, or an optionally substituted cycloalkylene having from 5 to 7 carbon atoms;

$Y_1$ selected from

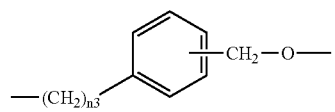

where n$_3$ is an integer from 0 to 3;

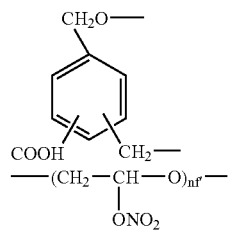

where nf' is an integer from 1 to 6, preferably from 2 to 4;

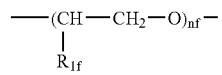

where $R_{1f}$=H, CH$_3$ and nf is an integer from 1 to 6, preferably from 2 to 4.

The compounds which can be mentioned, and which are those preferred, are the ones listed below where B can be obtained according to the known processes of the art.

For example, the precursors and related processes described for example in The Merck Index, 12th Ed. of 1996, herein incorporated by reference, can be mentioned as precursors and related processes. The precursors (according to the Merck nomenclature) include the following, where H$_2$, H, R, R', R" have the meaning as defined in the compounds listed below: budesonide, hydrocortisone, alclometasone, algestone, beclomethasone, betamethasone, chloroprednisone, clobetasol, clobetasone, clocortolone, cloprednol, cortisone, corticosterone, deflazacort, desonide, desoximetasone, dexamethasone, diflorasone, diflucortolone, difluprednate, fluazacort, flucloronide, flumethasone, flunisolide, fluocinolone acetonide, fluocinonide, fluocortyn butyl, fluocortolone, fluorometholone, fluperolone acetate, fluprednidene acetate, fluprednisolone, flurandrenolide, formocortal, halcinonide, halobetasol propionate, halometasone, halopredone acetate, hydrocortamate, loteprednol etabonate, medrysone, meprednisone, methylprednisolone, mometasone furoate, parametasone, prednicarbate, prednisolone, prednisolone 25-diethylaminoacetate, prednisolone sodium phosphate, prednisone, prednival, prednylidene, rimexolone, triamcinolone, triamcinolone acetonide, 21-acetoxypregnenolone, cortivazol, amcinonide, fluticasone proprionate, mazipredone, tixocortol, triamcinolone hexacetonide.

The X$_1$ connecting bridges as above defined are obtainable by using the methods known in the art as indicated above or by modifing the known methods by introducing X$_1$ bridges when these are different from the connecting bridges described in the listed patents, using processes known in the art. Generally the connection between B and X$_1$ is, as seen, of an ester or amide type (NH or $NR_{1C}$, as defined in X). Any well known synthetic route for forming these bonds can be used to form this connection.

In the case of esters, the most direct synthethic route includes: reaction of acyl chlorides B—CO—Cl in halogen alcohols of the HO—$Y_a$—Cl, HO—$Y_a$—Br, HO—$Y_a$—I- type, where $Y_a$ is equal to Y or $Y_1$ without the oxygen atom, in test conditions which are part of the known art.

The reaction products of formula B—CO—O—Y—Cl (Br,I) can also be obtained by reacting the sodium or potassium salts of salts acids B—CO—OH with dihalogen derivatives of the general formula $Y_aCl_2$, $Y_aBr_a$ or $Y_aI_2$, $ClY_aBr$, $ClY_aI$, $BrY_aI$.

The reaction products are converted into the final products by reacting with $AgNO_3$ in acetonitrile according to what is known in the literature.

The general scheme is as follows:

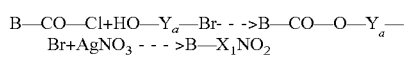

where $X_1 = Y_aO$.

The general scheme may also be as follows:

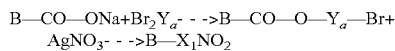

where $X_1 = Y_aO$.

In this case of amide, the synthetic sequence includes reaction of the same acyl chlorides BCOCl with aminoalcohols of the general formula $NH_2$—$Y_a$—OH, $NHR_{1C}$—$Y_a$—OH to give amides of the general formula:

B—CO—NH—$Y_a$—OH and B—CO—$NR_{1C}$—$Y_a$—OH according to known methods.

Reaction of these amides with halogenating agents such as, for example $PCl_5$, $PBr_3$, $SOCl_2$, etc., gives the halogen derivatives of the general formula:

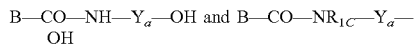

The latter give the final products $BX_1NO_2$ by reacting with $AgNO_3$ in acetonitrile according to methods known in the literature.

The sequence may be represented as:

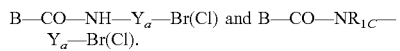

where $Y_aO$ is $X_1$.

An alternative route to ester formation is reaction of the sodium or potassium salts of the acids with the nitric esters of halogen alcohols of the general formula:

$NO_2$—O—$Y_a$—Cl(Br,I)

to directly give the products of the invention.
The reaction scheme is as follows:

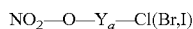

where $Y_aO$ is $X_1$.

Other synthetic routes similar to those described above include those in which the dihalogen derivative $Br_2Y_a$ is reacted with enolates. The reaction products are then converted by reacting with $AgNO_3$ in acetonitrile according to the above reaction. The general scheme is shown for an —OH in group B, of the type —$CH_2$—OH, =CH—OH, is as follows:

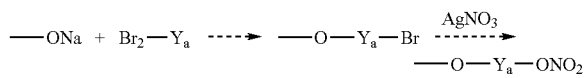

The processes to obtain these $X_1$ connecting groups are described in patent application WO95/30641 herein incorporated by reference.

As said above the compounds of the invention of formula B—$X_1$—$NO_2$ or their pharmaceutical compositions, are used for the treatment of diseases in which the well known corticoids products are employed.

In particular, it can be specifically mentioned the use in respiratory disorders, e.g. antiasthmatic, the use as antiarthritic, antipruritic, antipsoriatic, antieczematic; the use in vascular disorders, e.g. as angiostatic, the use in immunology disorders, e.g. as immunosoppressive.

The compounds, or their compositions, of the present invention can be administered for example by oral, rectal (intestinal disorders), parenteral route or by local (dermal, topical, transdermal, ocular, inhalatory, etc.) application.

The following examples are given only for illustrative purpose as an explanation but not as a limitation of the present invention.

EXAMPLE 1

Chemical Synthesis

Preparation of Hydrocortisone Nitroderivative (HCN)

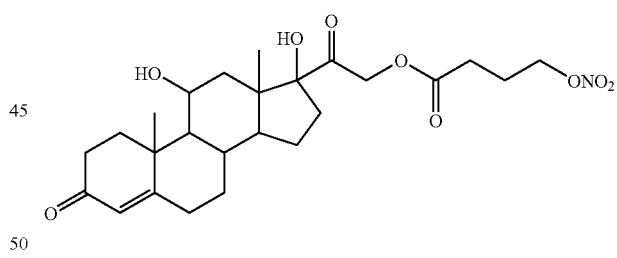

EXAMPLE 1A

Preparation of Hydrocortisone (4-chloro)butanoate

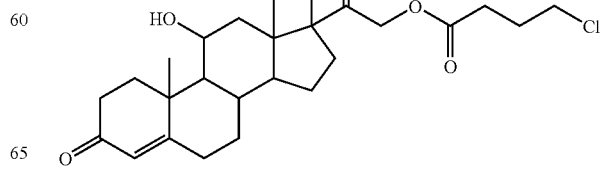

4 portions of 4-chlorobutanoylchloride (0.32 ml×4) and triethylamine (0.3 g×4) were added in 24 hours to a solution of hydrocortisone (1 g) in $CHCl_3$ dried over $P_2O_5$, and stirred for 3 days. The solution was treated with water, the organic phase was separated, dried ($Na_2SO_4$) and deprived of the solvent at reduced pressure. The crude residue was ground with hexane and $CH_2Cl_2$ to give a white solid with a 53% yield by weight, which had a melting point (m.p.) of 155° C.

The product was characterised by mass spectometry: $M^+$493.

$^1H$ NMR (300 MHz $CDCl_3$): 0.95 (3H,s,$CH_3$), 1.45 (3H, s, $CH_3$), 2.12 (2H, t, $CH_2$ in 2), 2.6 (2H, t, $CH_2COO$), 3.65 (2H, t, $CH_2Cl$), 4.45 (1H, m, C$\underline{H}$OH), 4.35 and 5.05 (2H, 2d, $COCH_2O$), 5.70 (1H, s, olefin H).

Preparation of Hydrocortisone (4-nitroxy)butanoate $AgNO_3$ (0.2 g) was added to a solution of hydrocortisone-4-chlorobutanoate prepared as above (0.23 g) in acetonitrile (70 ml) and refluxed for 16 hours. The solution was deprived of the solvent at reduced pressure and chromatographed on silica gel using a solution of ethyl acetate and $CH_2Cl_2$ (3:7) as an eluant.

Cortisone 4-nitroxybutanoate was recovered from the head fractions.

The product was characterised by $^1H$ NMR (300 MHz $CDCL_3$): 0.95 (3H, s, $CH_3$), 1.45 (3H, s, $CH_3$), 2.12 (2H, t, $CH_2$ in 2), 2.6 (2H, t, $CH_2COO$), 4.45 (1H, m, C$\underline{H}$OH), 4.45 (2H, t, $CH_2O-NO_2$), 4.35 and 5.05 (2H, 2d, $COCH_2O$), 5.68 (1H, s, olefin H).

EXAMPLE 1B

The product from Example 1A was also prepared using another synthetic route.

Preparation of Hydrocortisone 4-bromobutanoate

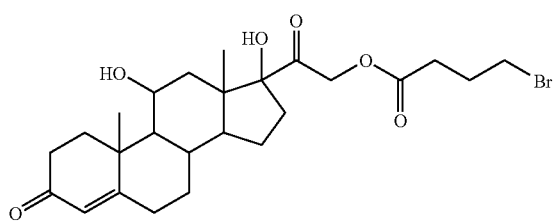

Five portions of 4-bromobutanoylchloride (0.35 ml×5) and potassium carbonate (0.4 g×5) were added in 24 hours to a solution of hydrocortisone (1 g) in $CHCl_3$ dried over $P_2O_5$ and stirred for 5 days. The solution was treated with water, the organic phase was separated, dried ($Na_2SO_4$) and deprived of the solvent at reduced pressure.

Preparation of Hydrocortisone 4-nitroxybutanoate (HCN)

$AgNO_3$ (0.2 g) was added to a solution of hydrocortisone 4-bromobutanoate prepared as above (0.23 g) in acetonitrile (70 ml) and stirred for 48 hours at room temperature.

The solution was deprived of the solvent at reduced pressure and chromatographed on silica gel using a solution of ethyl acetate and $CH_2Cl_2$ (3:7) as an eluant.

Cortisone 4-nitroxybutanoate was recovered from the head fractions and characterised by mass spectometry: $M^+$ 493. The spectrum was the same as that shown in Example 1A.

EXAMPLE 2

Evaluation of Safety and Activity

The products were administered in a 2%-by-weight carboxymethyl cellulose suspension during in vivo tests, while a 0.1%-by-weight dimethylsulphoxide suspension was used for in vitro studies.

The test groups always included 8 samples (except when differently stated in the examples) for adequate statistical evaluation, to be carried out when necessary according to common statistical procedures.

EXAMPLES 2A

Acute Toxicity Study

The acute toxicity of the product from Example 1A was roughly evaluated by orally administering a single dose of substance to a group of 10 mice of the Swiss strain.

Death incidence and appearance of toxic symptoms were observed during a period of 14 days after the compound administration.

The animals showed no sign of apparent toxicity even after administration of a 50 mg/kg dose.

EXAMPLE 2B

Study of Antiarthritic Activity

Adjuvant arthritis was induced in male rats of Lewis strain, weighing 170±15 g by intracaudal injection of 0.6 mg of Mycobacterium butyricum (Difco) suspended in 0.1 ml of mineral oil. The animals were treated with a vehicle made up of an intraperitoneal (i.p.) 2%-by-weight suspension of carboxymethyl cellulose in water, with intraperitoneal hydrocortisone of HCN (a suspension as described above) at doses of 5 mg/kg or doses of 10 mg/kg, starting from the first day after mycobacterium inoculation.

Arthritis development was assessed 21 days later. To the arthritic lesions an arbitrary score was assigned according to the following scale:
hind limbs: 0 to 7 for each (0 for no lesions and 7 for most severe lesions);
forelimbs: 0 to 4.5 for each (0 for no lesions and 4.5 for most severe lesions);
tail: 0 to 5 (0 for no lesions and 5 for most severe lesions),
ears: 0 to 2 for each (0 for no lesions and 2 for most severe lesions);
nose and eyes: 0 to 1 ofr each (0 for no lesions and 1 for most severe lesions).

The results were expressed as a percentage of inhibition compared to the value obtained in the control group (animals treated with the vehicle alone).

The result are shown in Table 1.

TABLE 1

STUDY OF ANTIARTHRITIC ACTIVITY OF COMPOUND HCN
VERSUS HYDROCORTISONE IN RATS

| COMPOUND | DOSE (mg/kg) | ANTIARTHRITIC ACTIVITY (%) |
|---|---|---|
| HYDROCORTISONE | 5 | 40 |
| HYDROCORTISONE | 10 | 55 |
| HCN | 5 | 45 |
| HCN | 10 | 62 |

As shown by the results in Table 1, the test products were capable of similarly inhibiting development of the arthritic process caused by mycobacterium. However, being the tolerability of HCN much higher than that of hydrocortisone (see ex 2C below), the results in terms of activity are much better in the case of HCN (see for comparison 40% of antiarthritic activity obtained with 5 mg/kg hydrocortisone with respect to 62% obtained with 10 mg/kg HCN).

EXAMPLE 2C

Study of Gastric Tolerability (Safety)

Male Sprague-Dawley rats fasted for 24 hours were treated with 5 to 10 mg/kg of intraperitoneal hydrocortisone or HCN.

Twenty-four hours later the animals were sacrificed, the stomach was removed and tissue was grossly examined for the presence of lesions as described by Del Soldato et al.: "The influence of fasting and cimetidine on the relationship between ulcerogenic and anti-inflammatory properties of cimetidine", Br. J. Pharmacol. 67, 33–37, 1979. The degree of severity of the disease was evaluated according to common methods and expressed as arbitrary values. The results are shown in Table 2.

TABLE 2

STUDY OF GASTRIC TOLERABILITY OF COMPOUND HCN
VERSUS HYDROCORTISONE IN RATS

| COMPOUND | DOSE (mg/kg) | GASTRIC TOLERABILITY |
|---|---|---|
| HYDROCORTISONE | 5 | 2.0 |
| HYDROCORTISONE | 10 | 3.5 |
| HCN | 5 | 0.5* |
| HCN | 10 | 1.2* |

Data are expressed as arbitrary values according to the following scale: 0 = absent; 1 = mild lesions; 2 = moderate lesions; 3 = punctiform ulcers; 4 = severe and numerous ulcers.
*P < 0.05 (where P is probability) compared to corresponding value in group treated with hydrocortisone.

As shown in Table 2, the rats treated with hydrocortisone exhibited a marked disease in the gastrointestinal tract, varying in severity from mucosal erosion to ulcer involving the muscle layer, wall adhesions, ascites, peritonitis. In the other groups treated with the vehicle alone or HCN, the damage was much lower or even absent.

EXAMPLE 2D

Study of Nitroxysynthetase Activity

The nitroxy-sinthetase inhibiting activity induced by lipopolysaccharide (LPS) was determined in rat neutrophils and stomach after administration of one of the test compounds and compared with that obtained after treatment with the suspending vehicle only. Wistar rats fasted for 24 hours before treatment received one of the test compounds intraperitoneally (10 mg/kg) or LPS intravenously (caudal vein) (5 mg/kg). Four hours later the animals were sacrificed. Blood for neutrophil isolation and stomach were removed.

Enzymatic activity was determined according to the method described by Assreuy et al.: "Feedback inhibition of nitric oxide synthase activity by nitric oxide", Br. J. Pharmacol. 108, 833–7, 1993. The results are shown in Table 3.

TABLE 3

STUDY OF NITROXYSYNTHETASE ACTIVITY IN COMPOUND
HCN VERSUS HYDROCORTISONE IN RATS

| COMPOUND | DOSE (mg/kg/i.p.) | NITROXYSYNTHETASE ACTIVITY[a] |
|---|---|---|
| VEHICLE | — | 100 |
| HYDROCORTISONE | 10 | 55* |
| HCN | 10 | 62* |

[a]percent inhibition compared to group treated with vehicle alone
*p < 0.05 compared to corresponding value in group treated with vehicle.

As shown by Table 3, both test products proved to be very effective in inhibiting nitroxysynthetase compared to the group treated with the vehicle alone.

EXAMPLE 2E

Study of Bone Toxicity

Bone tissues (parietal bone from rat foetus) grown in vitro according to the method described by Doherty et al. ("The effect of glucocorticoids on osteoblast function. The effect of corticosterone on osteoblast, expression of beta-I integrins", Journal of Bone and Joint Surgery, Series A77/3, 396–404, 1995) was used. Hydrocortisone or HCN or the vehicle were incubated at concentrations of 100 nmol.

Ninety six hours later calcium content and bone dry weight were measured.

The results are shown in Table 4.

TABLE 4

EFFECT OF HCN AND HYDROCORTISONE ON BONE GROWTH IN
RATS

| TREATMENT | (nmol) | Calcium $\Delta°$ % | DRY TISSUE WEIGHT $\Delta°$ % |
|---|---|---|---|
| VEHICLE | — | 310 | 160 |
| HYDROCORTISONE | 10 | 70* | 95* |
| HCN | 10 | 287 | 149 |

°Compared to initial value (incubation time zero)
*P < 0.05 compared to values obtained in control group (vehicle)

As shown in Table 4, a significant increase in tissue dry weight and increased calcium were observed after incubation with the vehicle or HCN. After incubation with hydrocortisone, the calcium content decreased and the bone dry weight did not increase. This shows that this treatment with hydrocortisone adversely affected bone growth.

EXAMPLE 2F

Study of Some Cardiovascular Parameters

The effect of the test products on some cardiovascular parameters was studied in conscious Long Evans rats (350 to 450 g) which were appropriately monitored, as described by Gardiner et al.: "Influence of dexamethasone on the regional haemodynamic responses to lipopolysaccharide in conscious rats: effect of the non-selective endothelin antagonist: SB 209670", Br. J. Pharmacology 117, 49P, 1996. The animals were treated with the vehicle (physiologic saline solution, 0.9% sodium chloride, s.c.) subcutaneous hydrocortisone or HCN (10 mg/kg). Heart rate and blood pressure were recorded 4 hours after treatment.

Table 5 shows the data obtained as per-cent variation from control values.

TABLE 5

STUDY OF COMPOUND HCN VERSUS HYDROCORTISONE IN SOME CARDIOVASCULAR PARAMETERS IN RATS

| COMPOUND | DOSE (mg/kg) | HEART RATE[a] (%) | BLOOD PRESSURE[b] |
|---|---|---|---|
| VEHICLE | — | 100 | 160 |
| HYDROCORTISONE | 10 | 89* | 115* |
| HCN | 10 | 98 | 103 |

*$P < 0.05$ compared to group treated with vehicle
[a]percent change compared to value recorded in group treated with vehicle alone (324 ± 7 beats per minute)
[b]percent change compared to value recorded in group treated with vehicle alone (101 ± 2 mm Hg)

The results in Table 5 show that the product of the invention HCN does not affect the cardiovascular parameters measured. On the contrary, hydrocortisone used in the known art shows significant pressure as well as cardiac changes.

EXAMPLE 2G

Study of Angiostatic Activity in Rats

Male Wistar rats weighing 180 to 200 g were used according to the procedure described by Andrade et al.: "Quantitative in vivo studies on angiogenesis in a rat sponge model", Brit. J. Exp. Pathol. 68, 755–766, 1987. The neovascularisation was evaluated in relation to blood flow by implanting a small sponge in the subcutaneous tissue for 14 days and determining $^{133}$Xe clearance. Briefly, an amount of $^{133}$Xe equal to 10 µl was injected into the sponge using a small polyethylene cannula. The residual radioactivity from implantation using a gamma ray detector and the $^{133}$Xe clearance for 6 minutes was measured as a percentage of the initial value. The validity of this method for measuring neovascularisation was recently demonstrated by HU et al.: "Correlation of $^{133}$Xe clearance, blood flow and histology in the rat sponge model for angionenesis. Further studies with angiogenic modifiers", Lab. Invest. 72, 601–610, 1995.

The test compounds were administered by the subcutaneous route at a dose of 10 mg/kg from day 1 to day 13 after implantation. $^{133}$Xe was measured at day 14 from subcutaneous implantation, the animals were then sacrificed and the weights of thymus and spleen were recorded.

Table 6 shows the data obtained regarding the effect of the test products on neovascularisation and on the weight of spleen and thymus.

TABLE 6

EFFECT OF HCN AND HYDROCORTISONE ON $^{133}$Xe CLEARANCE AND WEIGHT OF SPLEEN AND THYMUS AT DAY 14

| TREATMENT | $^{133}$Xe(%) | SPLEEN (mg) | THYMUS (mg) |
|---|---|---|---|
| VEHICLE | 42 | 663 ± 25 | 313 ± 28 |
| HYDROCORTISONE | 33 | 642 ± 32 | 185 ± 17* |
| HCN | 22* | 673 ± 38 | 297 ± 31 |

*$P < 0.05$ compared to values obtained in control group (vehicle)

As evident, HCN proved to be capable of exerting a marked angiostatic effect without changing the weight of spleen or thymus, differently from the reference product.

As it is clear from the whole of the data shown in Tables 1 to 6, the pharmacodynamic activity—anti-arthritic, immunosuppressive and antiangiogenic activities—and tolerability of the nitroderivative are superior than those of the corticoid from the known art.

EXAMPLE 3

Dexamethasone 21-(4-bromobutyrate) [II]

| Dexamethasone [I] | 3.5 g | 8.9 mmol |
|---|---|---|
| 4-Bromobutyryl chloride | 4.06 ml | 35 mmol |
| Potassium carbonate | 4.9 g | 35 mmol |
| Tetrahydrofuran | 70 ml | |

The solution of compound I in tetrahydrofuran is portion-wise treated with 4-bromobutyryl chloride (0.81 ml×5) and potassium carbonate (0.98 g×5) during 7 hours. The mixture is stirred overnight, the solvent is evaporated under vacuum and the residue is treated with ethyl ether and water. The organic layer is separated, washed with water and dried with anhydrous sodium sulfate. After evaporation of the solvent, the residue is purified by silica gel flash column chromatography eluting with t.butyl methyl ether-hexane 1-1 to give:
less polar compound 1.0 g;
derivative II 1.5 g (m.p. 184–187° C.; yield 31%)
TLC: t.butyl methyl ether-hexane 2-1.

Dexamethasone 21-(4-nitrooxybutyrate) [III] (Compound DXN)

| Compound II | 1.5 g | 2.7 mmol |
|---|---|---|
| Silver nitrate | 2.4 g | 14.1 mmol |
| Acetonitrile | 250 ml | |

The mixture of compound II and silver nitrate in acetonitrile is refluxed for 7 hours. After filtration of inorganic salts, the solvent is evaporated under vacuum and the residue is treated with ethyl ether. The organic layer is twice washed with water, dried with anhydrous sodium sulfate and evaporated under vacuum. The residue is poured into ethyl ether and filtered to give 1.27 g of pure compound III as a white solid (m.p. 183–185° C.; yield 90%)
TLC: t.butyl methyl ether-hexane 2-1.
The following forms are enclosed:
synthetic scheme;

NCX 1005 batch 1;
NCX 1005/1 analysis.

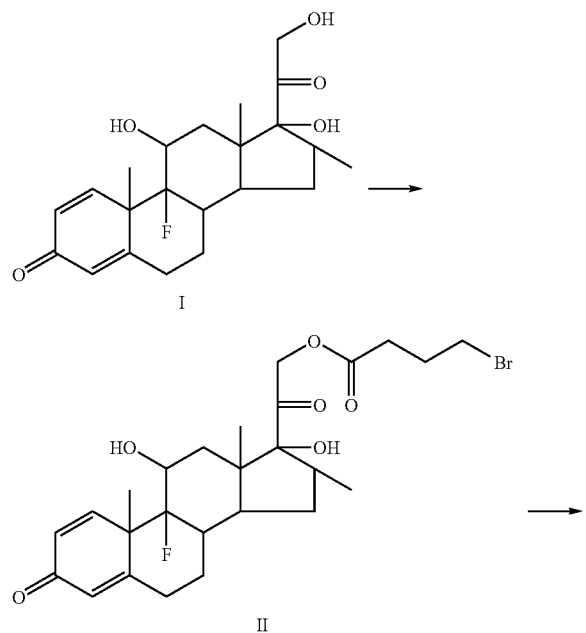

SINTHEIC SCHEME FOR THE PREPARATION OF DEXAMETHASONE 21(4-NITROOXIBUTYRATE)

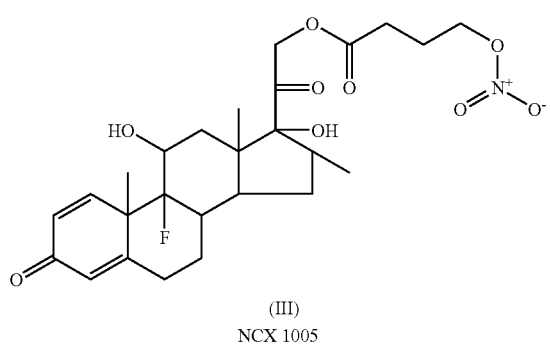

(III)
NCX 1005

EXAMPLE 4

Study of the Activity on Leucocyte Accumulation

Male Swiss albino mice (27–33 g) maintained on a standard chow pellet diet and tap water ad libitum were used. The experiment was done as previously described by Perretti et al. (Perretti M., Solito E., Parente L., "Evidence that endogenous interleukin-1 is involved in neutrophil migration in acute experimental inflammation in rats and mice", Agents Actions, 35, 71, 1992). Animals were pretreated with zymosan (1 mg/0.5 ml) i.p. at time 0. Two hours later DEXAMETHASONE (1 mg/kg) (Ex3-I), DXN (Ex3-III) (1 mg/kg) or phosphate buffered saline (PBS) was given intravenously. The animals were sacrificed at 4 and 24 h the lavage fluids were collected and differential cell counts were performed following staining in Turk's.

Table 7 reports results obtained on the inhibitory effect of the tested compounds on zymosan-induced leucocyte migration in mice. As can be observed the nitroderivative steroid is much more active than dexamethasone.

TABLE 7

| Inhibition of neutrophil and monocyte recruitement by DEXAMETHASONE and DXN (1 mg/kg) given 2 h i.v. after zymosan (1 mg/0.5 ml) i.p. | | | | |
|---|---|---|---|---|
| treatment | PMN × $10^6$/mouse (time 4 h) | % reduction | mono-mØ × $10^6$/ mouse (time 24 h) | % reduction |
| vehicle | 10.1 ± 1.0 | — | 8.8 ± 1.3 | — |
| DXN | 4.5 ± 0.3 | 55.4 | 4.5 ± 0.6 | 48.8 |
| DEXAMETHASONE | 6.4 ± 0.4 | 36.6 | 6.3 ± 0.2 | 28.4 |

EXAMPLE 5

Study of the Anti-proliferative Activity in Human Airway Smooth Muscle Cells

Human airway smooth muscle cells were cultured by standard explant methods. Tissues were collected into sterile pots containing PBS and penicillin and streptomycin. Under sterile tissue culture conditions, tissues were cut into small pieces (approximately 1 mg weight) and placed into standard medium containing 20% fetal calf serum (FCS) for several days (medium changed every 2–4 days). $^3$H-thymidine was measured in the DNA fraction of cells cultured into 48 well plates. Cells were cultured to confluence in the medium containing 10% FCS. Cells were deprived of serum for 24 h before the addition of 10% FCS, together with different concentration of steroids. After 24h, $^3$H-thymidine was added to the cells for 4h. Cells were washed with phosphate buffered saline and ethanol. The DNA was extracted with sodium hydroxide solution and the $^3$H material counted by scintillation. The data represent observations made in triplicate wells from smooth muscle cultured from one healthy lung donor. Table 8 reports results obtained on the inhibitory effect of the tested compounds on human airway smooth cell proliferation. As can be observed the nitroderivative steroid is much more active than dexamethasone.

TABLE 8

Inhibition of human airway smooth cell mitogenesis by different concentrations of DEXAMETHASONE and DXN

| Treatment | Concentration (logM) | $^3$H-thymidine (CPM × 1000) |
|---|---|---|
| DEXAMETHASONE | −5 | 14.1 |
|  | −7 | 15.0 |
| DXN | −5 | 10.8 |
|  | −7 | 12.6 |

Conclusions

As can be observed from results reported above, both activity and safety of the new nitroderivatives are better than those owned by the precursor steroids.

The invention claimed is:
1. A compound of formula

B—R''—X$_1$—NO$_2$ or their esters or salts,
wherein B—R'' has the following structure:

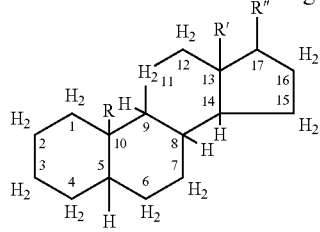

R'' is —(CO—L)$_t$—(X)$_{t1}$ wherein in the place of H in the CH group or H$_2$ in the CH$_2$ group there may be the following substituents:
at position 1-2: a double bond;
at position 2-3

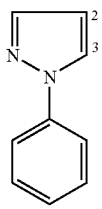

at position 2, Cl or Br;
at position 3, oxo, —O—CH$_2$—CH$_2$—Cl, or OH;
at position 4-5, a double bond;
at position 5-6, a double bond;
at position 6, Cl, F CH$_3$, or CHO;
at position 7, Cl;
at position 9, Cl or F;
at position 11, OH, oxo or Cl;
at position 16, CH$_3$, OH, or =CH$_2$;
at position 17, OH, CH$_3$, OCO(O)$_{ua}$(CH$_2$)$_{va}$CH$_3$, or

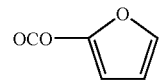

wherein ua is an integer equal to 0 or 1 and va is an integer from 0 to 4;
at position 16-17,

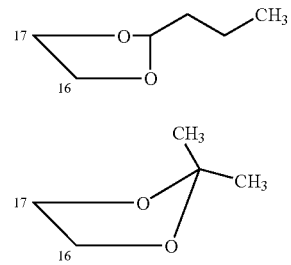

R and R' are equal or different one from the other and may be hydrogen or linear or branched alkyls having from 1 to 4 carbon atoms,
wherein in R'' t and t1 are integers where t is equal to 1, t1 equals 0, 1;
wherein between B and X$_1$ there is an ester or amide linkage;
the bivalent bridging member L is selected from the group consisting of (CR$_4$R$_5$)$_{na}$(O)$_{nb}$(CR$_4$R$_5$)$_{n'a}$(CO)$_{n'b}$(O)$_{n''b}$ (CO)$_{n'''b}$(CR$_4$R$_5$)$_{n''a}$, wherein na, n'a, and n''a are equal to or different one from the other and are integers from 0 to 6, nb, n'b, n''b and n'''b are equal to or different to each other and are equal to 0 or 1; R$_4$ and R$_5$ are equal or different one from the other and are selected from the group consisting of H, linear or branched alkyls having 1 to 5 carbon atoms, X is equal to Xo where Xo is O, NH, NR$_{1c}$ where R$_{1c}$ is a linear or branched alkyl having from 1 to 10 carbon atoms;
X$_1$ is selected from the group consisting of

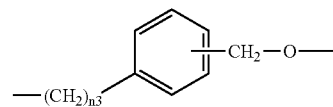

wherein n$_3$ is an integer from 0 to 3; and

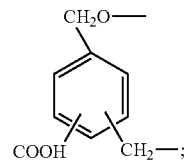

wherein B is a residue of betamethasone.
2. Pharmaceutical composition comprising a compound according to claim 1 and a pharmaceutically acceptable carrier.

* * * * *